United States Patent [19]

Pavlinch

[11] 4,239,044
[45] Dec. 16, 1980

[54] INFLATABLE CATHETER FOR A MALE URINAL

[76] Inventor: George R. Pavlinch, P.O. Box "P", Murrieta, Calif. 92362

[21] Appl. No.: 364

[22] Filed: Dec. 29, 1978

[51] Int. Cl.³ .............................................. A61F 5/44
[52] U.S. Cl. .................................... 128/295; 128/760; 128/764; 128/765; 128/767
[58] Field of Search ............... 128/294, 295, 760, 763, 128/765, 766, 767

[56] References Cited

U.S. PATENT DOCUMENTS

| 2,686,519 | 8/1954 | Westerman | 128/294 |
| 2,699,781 | 1/1955 | Koch | 128/295 |
| 3,511,241 | 5/1970 | Lee | 128/295 |

FOREIGN PATENT DOCUMENTS

| 2742298 | 3/1978 | Fed. Rep. of Germany | 128/295 |
| 946822 | 6/1949 | France | 128/294 |

Primary Examiner—William E. Kamm
Assistant Examiner—J. L. Kruter

Attorney, Agent, or Firm—Fischer and Tachner

[57] ABSTRACT

A compact and inexpensive air catheter having particular application as an improved male incontinence device. The catheter herein disclosed includes a relatively thick outer tubular sheathing and a collapsible, relatively thin inner tubular sheathing. Inner and outer sheathings are concentrically arranged relative to one another. The region of the catheter between the inner and outer sheathings forms an annular air chamber, which chamber is adapted to be inflated, under pressure, in order to collapse the inner sheathing around a user's organ, whereby an efficient air and liquid-tight seal is formed therewith, regardless of the shape or size of the organ. The region of the catheter that is defined by the interior of the inner sheathing forms an axially extending urine drain passage for the purpose of conveying the user's urine to an external urine collection means. During operation, the drain passage is substantially air evacuated, whereby the possibility of urine backflow thereto, under the influence of gravity, from the collection means is substantially eliminated.

12 Claims, 4 Drawing Figures

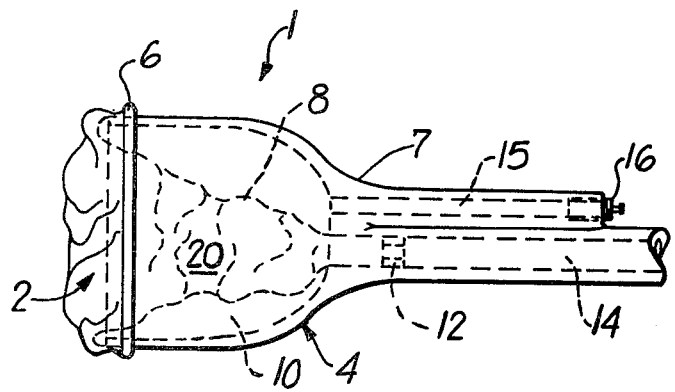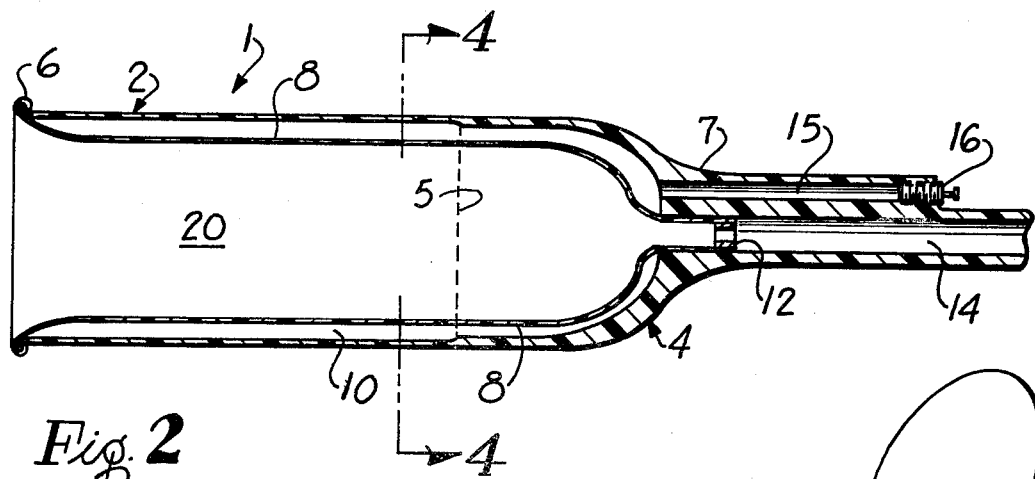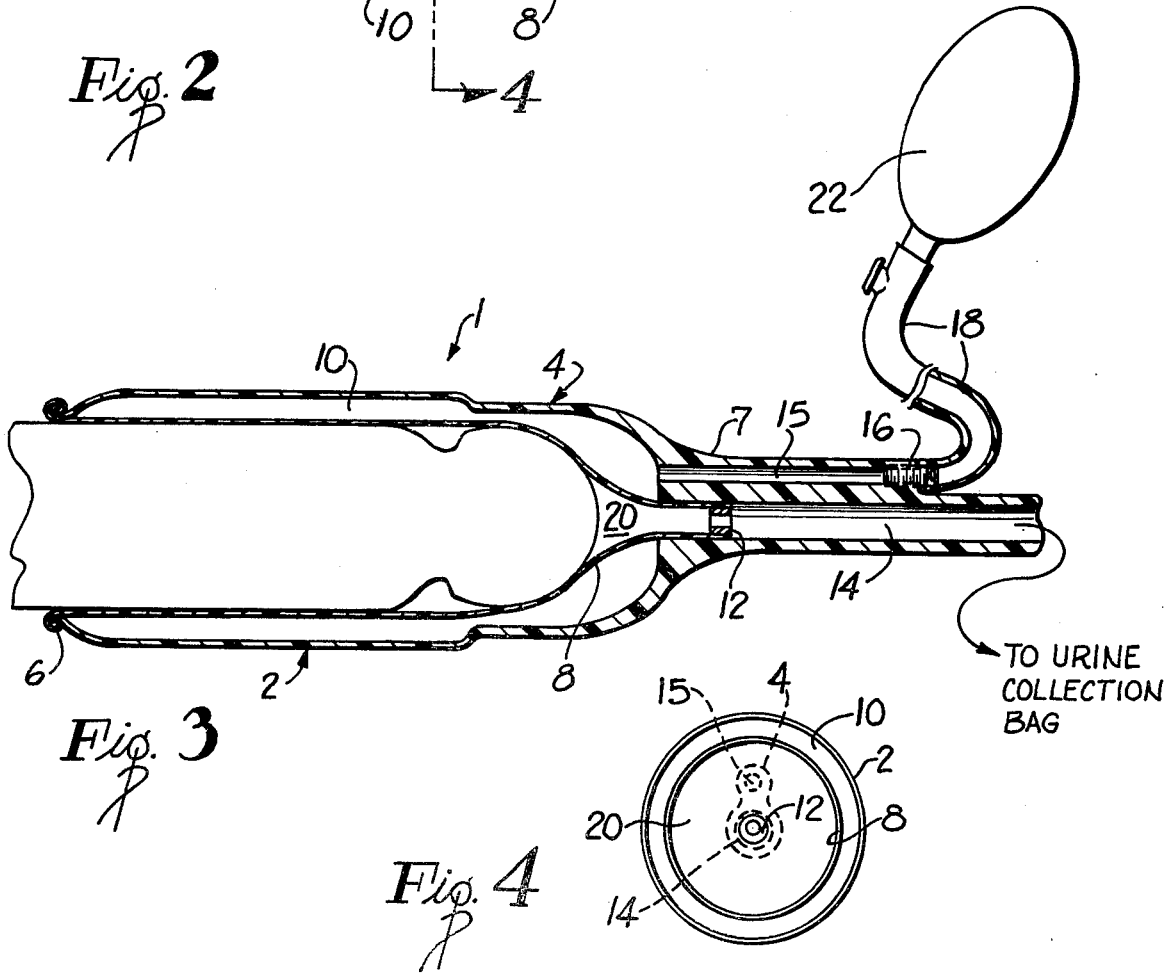

INFLATABLE CATHETER FOR A MALE URINAL

BACKGROUND OF THE INVENTION

1. Field of the Invention

This invention relates to a compact and inexpensive inflatable catheter having particular application as an improved male incontinence device.

2. Statement of the Prior Art

As will be known to those skilled in the art, disabled, or otherwise handicapped persons, often times do not have sufficient control of their bodily functions so as to be capable of adequately restraining the discharge of urine. As a result, several incontinence devices have been designed to assist handicapped male patients with the collection and disposal of urine. By way of example, the following U.S. patents are illustrative of conventional incontinence devices which may be utilized by a male patient so that both the voluntary and involuntary discharge of urine may be suitably disposed of:

U.S. Pat. No. 2,699,781; Jan. 18, 1955; Koch.
U.S. Pat. No. 3,353,538; Nov. 21, 1967; Carrigan.
U.S. Pat. No. 3,916,902; Nov. 4, 1975; Lineberger.

However, by the nature of their construction, the prior art incontinence devices are not adapted to adequately fit different male organs having various sizes and shapes. As a result, the prior art incontinence devices may be difficult to secure to the user's organ and are, therefore, incapable of providing a suitable fluid-tight seal therewith. Moreover, once attached, the prior art incontinence devices may fall off during use. To overcome these problems, many of the prior art incontinence devices are typically combined with external belts, adhesives, supporter-type articles, or the like. Consequently, these prior art devices are cumbersome and, accordingly, may be difficult for a handicapped person to apply without outside assistance. What is more, the expense of fabricating such devices is relatively high.

The configuration of the prior art incontinence devices may also promote the formation of pockets adjacent the end of the user's organ. Such pockets can result in the pooling of urine which may cause user discomfort as well as unsanitary conditions that typically lead to the formation of abscesses and the like.

Nothing is known in the prior art which shows or suggests a male urinal comprising a catheter having inner and outer tubular sheathings concentrically arranged with respect to one another so as to form an annular inflatable air chamber and an axial urine drain passage, each of which chamber and passage extending longitudinally through the body of the claimed catheter so as to have substantially identical linear dimensions. Hence, unlike that disclosed and claimed below, none of the prior art incontinence devices includes a urine drain passage which is substantially air evacuated so that an efficient air and liquid-tight seal is formed around the user's organ, whereby the catheter is securely attached to the organ, regardless of the size or shape thereof. Moreover, unlike that claimed below, none of the prior art incontinence devices is adapted to operate with suction as a one-way fluid valve for extracting urine, whereby the possibility of urine backflow, under the influence of gravity, from an external urine collection bag is substantially eliminated.

SUMMARY OF THE INVENTION

Briefly, and in general terms, a compact and inexpensive air catheter having application as an improved male incontinence device is disclosed. The catheter comprises a relatively thick tubular outer sheathing and a relatively thin tubular inner sheathing that is adapted to receive the user's organ. The inner and outer tubular sheathings are joined to one another at opposite ends of the catheter. In accordance with the present invention, an inflatable air chamber of annular cross-section is formed between the inner and outer sheathings. An axially extending urine drain passage is defined by the interior region of the inner sheathing. Both the air chamber and the urine drain passage have substantially identical linear dimensions through the body of the catheter.

The air catheter of the present invention also includes an air intake tube and a urine discharge tube. In operation, the air intake tube is connected between the air chamber and a source of air, whereby the chamber may be selectively inflated. The urine discharge tube is connected between the urine drain passage and an external urine collection bag, whereby urine may be collected and disposed of. The inflation of the air chamber via the air intake tube causes the relatively thin inner sheathing to collapse around a male organ inserted therein so that an efficient air and liquid-tight seal is formed with the organ, regardless of the shape or size thereof. By virtue of the collapsing air chamber, the urine drain passage becomes substantially devoid of air. Hence, the evacuated drain passage functions as a one-way fluid valve to prevent the backflow of urine, under the influence of gravity, from the external collection bag, regardless of the position of the bag. Moreover, any trickles or remnants of the user's urine is conveyed to the collection bag by means of suction created within the evacuated urine drain passage.

BRIEF DESCRIPTION OF THE DRAWINGS

FIG. 1 is a side elevational view of the air catheter of the present invention in a rolled-up, uninflated condition.

FIG. 2 is a partially sectioned, elevational view of the catheter of the present invention in an unrolled, uninflated condition.

FIG. 3 is a partially sectioned, elevational view of the catheter of the present invention applied to a male user's organ in an inflated condition for operation as an incontinence device.

FIG. 4 is a cross-section taken along the lines 4—4 of FIG. 2.

DESCRIPTION OF THE PREFERRED EMBODIMENT

Referring concurrently to FIGS. 1 and 2 of the drawings, the compact, inflatable air catheter 1, which forms the present invention, is illustrated. The catheter herein disclosed has particular application as an improved, light-weight, low cost, portable incontinence device for a handicapped, or otherwise disabled, male user. More particularly, FIG. 1 shows the air catheter 1 in a rolled-up, uninflated condition that is ready for easy application to the organ of the handicapped male user. Moreover, the catheter 1 is conveniently packaged or stored in the rolled-up condition. FIG. 2 shows the air catheter 1 in an unrolled and uninflated condition.

In accordance with the present invention and, as best illustrated in FIG. 2, catheter 1 has an elongated tubular body comprising a source member 2, that is adapted to receive the user's organ at a receiving end 6 thereof, and a drain member 4, that is adapted to convey the user's urine to an external collection bag from a tapered discharge end 7 thereof. Each of the source and drain members 2 and 4 are fabricated from a liquid impervious, flexible tubular sheathing, such as that consisting of a silicon or latex material. The receiving end 6 of source member 2 comprises a tightly rolled-up lip which enables catheter 1 to be easily fitted over the user's organ. By way of example, the drain member 4 may be similar to a conventional Penrose Drain, the details of which will be known to those skilled in the art. As is also best illustrated in FIG. 2, the source and drain members 2 and 4 are adhered to one another along a seam 5 by means of glue or similar adhesive. The seam 5 is formed at approximately the midsection of the unrolled catheter 1.

An elastic, inflatable inner tubular sheathing 8 is concentrically positioned within catheter 1 relative to the tubular sheathings that form source and drain members 2 and 4. In a preferred embodiment of the invention, the respective sheathings that form source member 2 and drain member 4 are substantially thicker than that which forms inner tubular sheathing 8, the advantage of which will be disclosed hereinafter. By way of example, the source sheathing 2 has a thickness of approximately 0.020 inches, the drain sheathing 4 has a thickness of approximately 0.053 inches, while the inner sheathing 8 has a thickness of approximately 0.0025 inches.

One end of inner sheathing 8 terminates in the formation of the rolled-up lip that comprises the receiving end 6 of source member 2. The second end of inner sheathing 8 is connected to the discharge end 7 of drain member 4 by a retaining means that is to be hereinafter disclosed, whereby an axially extending air chamber 10 of annular cross-section is formed between the inflatable inner sheathing 8 and the source and drain sheathings 2 and 4. The area within catheter 1, as defined by the interior of tubular sheathing 8, forms an axial drain passage 20 for the purpose of conveying the user's urine to an external collection bag. Unlike incontinence devices of the prior art, and as clearly shown in FIG. 2, each of air chamber 10 and drain passage 20 extends longitudinally throughout the tubular body of catheter 1, whereby chamber 10 and passage 20 have a substantially identical linear dimension.

The tapered discharge end 7 of drain member 4 interfaces with one end of each of a urine discharge tube 14 and an air intake tube 15. Tubes 14 and 15 may be integrally formed with one another and with the tapered discharge end 7 of drain member 4, so that the drain member 4 is constructed as a single piece. The first end of discharge tube 14 communicates with urine passage 20, and the first end of intake tube 15 communicates with air chamber 10. The second end of discharge tube 14 is connected to a suitable urine collection bladder bag (not shown), so as to facilitate the sanitary collection and disposal of the user's urine. Tubes 14 and 15 may be fabricated from any suitably flexible material, such as, for example, molded rubber, which material has a thickness that is sufficient to prohibit undesirable twisting or bending and possible blockage of the flow of urine through drain passage 20. By way of example, urine discharge tube 14 and air intake tube 15 are fabricated with identical thicknesses of 0.053 inches. However, it is preferable that, in order to accomodate rapid urine discharge, urine discharge tube 14 is formed with a substantially larger diameter than that of air intake tube 15.

The second end of inner sheathing 8 is glued around the outer periphery of a hollow, disc shaped insert 12, and the insert 12 is positioned inside the first end of urine discharge tube 14. Insert 12 is dimensioned so as to securely fit within discharge tube 14. However, a suitable adhesive may additionally be used to retain insert 12 and the second end of inner sheathing 8 within tube 14. Typically, insert 12 is fabricated from any rigid, liquid impervious material, such as, for example, a suitable plastic. A central recess or slot is cut into insert 12, so that the user's urine can pass therethrough from drain passage 20 to discharge tube 14. The respective alignments and sizes of axial air chamber 10, urine drain passage 20, urine discharge tube 14, air intake tube 15, and insert 12 within catheter 1 are best illustrated in FIG. 4 of the drawings.

The inflation of axially extending air chamber 10 is selectively controlled by means of a conventional one-way air intake valve 16. Air intake valve 16 is particularly sized so as to securely fit within the second end of air intake tube 15. As will be explained in greater detail while referring to FIG. 3 of the drawings, air intake valve 16 is adapted to be connected to a source of air so as to be capable of providing a supply thereof, under pressure, to air chamber 10 for the purpose of inflating chamber 10.

The operation of the presently disclosed air catheter 1 by a disabled user is described while referring to FIG. 3 of the drawings. Air intake valve 16 is connected to a source of air by means of a flexible tubing 18. The source of air may be a conventional hand operated air pump bulb 22, or the like. The user fits the uninflated, rolled-up source member 2 (as illustrated in FIG. 1) of catheter 1 over his organ. The source member 2 is unrolled to a desired length according to the size of the user's organ. Axially extending air chamber 10 is inflated by means of squeezing bulb 22 so that a stream of air is supplied to chamber 10 via tubing 18, one-way intake valve 16, and intake tubing 15. Inasmuch as the inner sheathing 8 is substantially thinner than both the source sheathing 2 and the drain sheathing 4, the air pressure in chamber 10 causes inner sheathing 8 to compress against the user's organ, regardless of the size or shape thereof. Therefore, inner sheathing 8 collapses until an efficient air and liquid-tight seal is formed around the user's organ, so that catheter 1 will not fall off during use.

By virtue of the similarity of the linear dimension of the longitudinally extending air chamber 10 and drain passage 20 throughout the tubular body of catheter 1, the compression of inner sheathing 8 causes urine drain passage 20 to become substantially devoid of air when urine discharge tube 14 is connected to the collection bag. Hence, and unlike the capabilities of prior art incontinence devices, the flow of heavier than air urine creates a suction effect in drain passage 20, so that any urine residue therein is efficiently extracted therefrom. Even more unlike the characteristics of any known prior art incontinence device, catheter 1 functions as a one-way fluid valve for the conveyance of urine between drain passage 20 and the urine collection bag. Inasmuch as compressed drain passage 20 is substantially air evacuated, the possibility of urine backflow from the collection bag to the user's organ, under the influence of gravity, is substantially eliminated, regardless of the position of the urine collection bag with respect to catheter 1. In addition, the secure fit of inner sheathing 8 around the user's organ substantially reduces the liklihood of urine pooling, a problem typically associated with many prior art incontinence devices. The undesirable collection or pooling of urine around the user's organ has heretofore resulted in user discomfort as well as unsanitary conditions.

The compact and lightweight characteristics of the presently disclosed improved air catheter 1 makes the application and operation thereof a relatively simple matter for the handicapped or disabled user without the necessity of additional assistance. Moreover, the present catheter 1 is securely retained on the user's organ without the additional requirement of cumbersome external belts, adhesives, or jockstrap supporter-type apparatus, all of which are common to many of the prior art incontinence devices. As a result, the present catheter 1 is manufactured with reduced costs while overcoming the problems inherent in prior art incontinence device configurations.

It will be apparent that while a preferred embodiment of the invention has been shown and described, various modifications and changes may be made without departing from the true spirit and scope of the invention.

Having thus set forth a preferred embodiment of the invention, what is claimed is:

1. A male incontinence device having a receiving end adapted to be applied to a user's organ and a drain end adapted to convey the user's urine to an external urine collection means, said incontinence device comprising:
    an outer tubular sheathing formed from a flexible material,
    an inner tubular sheathing formed from a flexible material,
    said inner and outer tubular sheathings joined together at each of the device receiving and drain ends, such that an annular, inflatable fluid chamber is formed between said inner and outer sheathings and an axially extending urine drain passage is formed at the interior of said inner sheathing, said fluid chamber and said drain passage having substantially identical linear dimensions through said device,
    urine conveying means having a relatively narrow diameter with respect to said urine drain passage to interconnect said inner tubular sheathing to said urine collection means, whereby to cause said inner sheathing to constrict at the drain end of said device, and
    fluid source means adapted to be connected to said fluid chamber for inflating said chamber, whereby said inner sheathing is collapsed under pressure around the user's organ and said drain passage is evacuated, so that urine is extracted therefrom by means of suction when said device is connected to the urine collection means and urine backflow from the collection means to said drain passage is prohibited.

2. The incontinence device recited in claim 1, wherein said inner and outer tubular sheathings are aligned in a substantially concentric relationship with respect to one another between said device receiving and drain ends.

3. The incontinence device recited in claim 1, wherein said outer sheathing is substantially thicker than said inner sheathing.

4. The incontinence device recited in claim 3, wherein said outer sheathing is approximately at least 10 times thicker than said inner sheathing.

5. The incontinence device recited in claim 1, wherein each of said fluid chamber and said urine drain passage extends longitudinally in and substantially through the entire length of said device.

6. The incontinence device recited in claim 1, further including a urine discharge tube and a fluid intake tube,
    said urine discharge tube forming the urine conveying means of relatively narrow diameter to interconnect said inner tubular sheathing to said urine collection means, and
    said fluid intake tube connected between said inflatable fluid chamber and said fluid source means.

7. The incontinence device recited in claim 6, wherein said fluid intake tube, said urine discharge tube, and the drain end of said device are integrally connected to one another so as to be constructed as a single piece.

8. The incontinence device recited in claim 6, further including one-way fluid valve means, said one-way valve means particularly dimensioned so as to be positioned securely within said fluid intake tube between said fluid source means and said fluid chamber so as to control the supply of fluid therebetween.

9. The incontinence device recited in claim 6, further including a hollow insert particularly dimensioned so as to be positioned securely within said urine discharge tube between said urine drain passage and the urine collection means so that the user's urine is conveyed therethrough,
    the drain end of said inner tubular sheathing being retained in said urine discharge tube by means of said insert, whereby to cause said inner sheathing to constrict.

10. The incontinence device recited in claim 1, wherein said urine conveying means having a relatively narrow diameter is a urine discharge tube,
    the drain end of said inner tubular sheathing connected at the interior of said urine discharge tube whereby to cause said urine drain passage to constrict.

11. A male urinal having a tubular body portion and comprising:
    an elastic inner tubular sheathing adapted to receive a user's organ at a first end thereof and to expel the user's urine at a second end thereof,
    a flexible outer tubular sheathing connected to the inner sheathing at the first and second ends thereof and aligned in a substantially concentric relationship therewith so that an inflatable, annular fluid chamber is formed between said inner and outer sheathings and an axially extending urine discharge passage is formed at the interior of said inner sheathing,
    each of said fluid chamber and said discharge passage extending longitudinally and completely through the tubular body portion of said urinal so as to have substantially identical linear dimensions therein,
    means to substantially narrow the diameter of said longitudinally extending urine discharge passage at the second end of said inner tubular sheathing relative to the diameter of said passage at the first end of said inner sheathing, so that pooling of urine within said passage is substantially eliminated, and
    fluid duct means connected to said fluid chamber and adapted to supply fluid thereto for the purpose of inflating said fluid chamber and collapsing said inner sheathing under pressure around the user's organ, whereby air is evacuated from said urine discharge passage, so that an efficient liquid-tight seal is formed around the user's organ.

12. The male urinal recited in claim 11, wherein said means to narrow said urine discharge passage comprises hollow disc means having an outside diameter that is less than the diameter of the urine discharge passage formed by the first end of said inner tubular sheathing, the second end of said inner tubular sheathing interconnected with said disc means so as to convey the user's urine thereto via said urine discharge passage.

* * * * *